United States Patent [19]

Carlier et al.

[11] Patent Number: 4,822,792
[45] Date of Patent: Apr. 18, 1989

[54] SUBSTITUTED 3-PIPERIDINAMINES OR 3-AZEPINAMINES, THE PREPARATION THEREOF AND THEIR APPLICATIONS IN THERAPY

[75] Inventors: Patrick Carlier, Chatel-Guyon; Jacques A. Simond, Les-Martres-de-Veyre; André J. Monteil, Chatel-Guyon, all of France

[73] Assignee: Riom Laboratoires C.E.R.M., Riom, France

[21] Appl. No.: 136,302

[22] Filed: Dec. 22, 1987

[30] Foreign Application Priority Data

Dec. 23, 1986 [FR] France ................... 86 18083

[51] Int. Cl.[4] .................. A61K 31/445; C07D 211/92
[52] U.S. Cl. ..................... 514/212; 514/329; 540/605; 540/606; 546/223; 546/224
[58] Field of Search .............. 540/605, 606; 546/223, 546/224; 514/212, 329

[56] References Cited

U.S. PATENT DOCUMENTS

| | | | |
|---|---|---|---|
| 3,998,834 | 12/1976 | Janssen et al. | 546/224 |
| 4,097,481 | 6/1978 | Banitt et al. | 546/234 |
| 4,208,418 | 7/1980 | Sanczuk et al. | 546/224 |
| 4,584,303 | 4/1986 | Huang et al. | 546/224 |

FOREIGN PATENT DOCUMENTS 0130957 10/1980 Japan ................... 540/606

*Primary Examiner*—Mary C. Lee
*Assistant Examiner*—Zinna Northington
*Attorney, Agent, or Firm*—William M. Blackstone

[57] ABSTRACT

Compounds of formula:

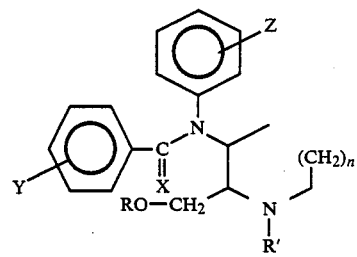

in which R and R' each denote an alkyl or cycloalkyl radical having 1 to 7 carbon atoms; X denotes —O— or $H_2$; and Y and Z denote hydrogen or one or more radicals chosen from halogeno, hydroxy, straight or branched alkyl having 1 to 6 carbon atoms, alkoxy having 1 to 6 carbon atoms, trifluoromethyl or methylenedioxy; n being able to assume the values 2 or 3; and their pharmaceutically acceptable salts.

Application as a cardiovascular medicinal product.

5 Claims, No Drawings

SUBSTITUTED 3-PIPERIDINAMINES OR 3-AZEPINAMINES, THE PREPARATION THEREOF AND THEIR APPLICATIONS IN THERAPY

The present relates to new substituted 3-piperidinamines or 3-azepinamines, the preparation thereof and their applications in therapy.

More precisely, the substituted 1-alkyl-2-alkoxymethyl-N-phenyl-N-(benzyl or benzoyl)-3-piperidinamines or -3-azepinamines according to the invention correspond to the following general formula:

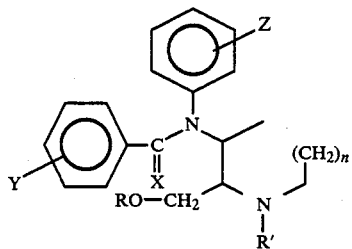

in which R and R' each denote an alkyl or cycloalkyl radical having 1 to 7 carbon atoms; X denotes —O— or H$_2$; and Y and Z denote hydrogen or one or more radicals chosen from halogeno, hydroxy, straight or branched alkyl having 1 to 6 carbon atoms, alkoxy having 1 to 6 carbon atoms, trifluoromethyl or methylenedioxy; n may assume the values 2 or 3.

The invention also relates to the salts of the said compounds with pharmaceutically acceptable organic or inorganic acids, such as hydrochloric, fumaric, maleic, citric or succinic acid, these acids being menioned only by way of illustration and without representing a limitation.

According to a preferred embodiment, the substituent R denotes one of the radicals isobutyl, methyl or cyclohexyl, and R' denotes a methyl or n-propyl radical.

Since the compounds of the invention contain asymmetric carbon atoms, racemic and/or separate optically active isomers as well as mixture thereof form part of the invention.

Pharmacological studies showed that the compounds of the invention possessed advantageous properties, enabling them to be applied in human therapy in the treatment of cardiovascular disorders.

The compounds of the invention can be prepared starting with a 2-(α-hydroxy-β-alkoxyethyl)-pyrrolidine or -piperidine, according to the reaction scheme below:

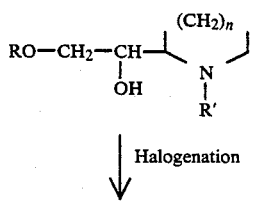

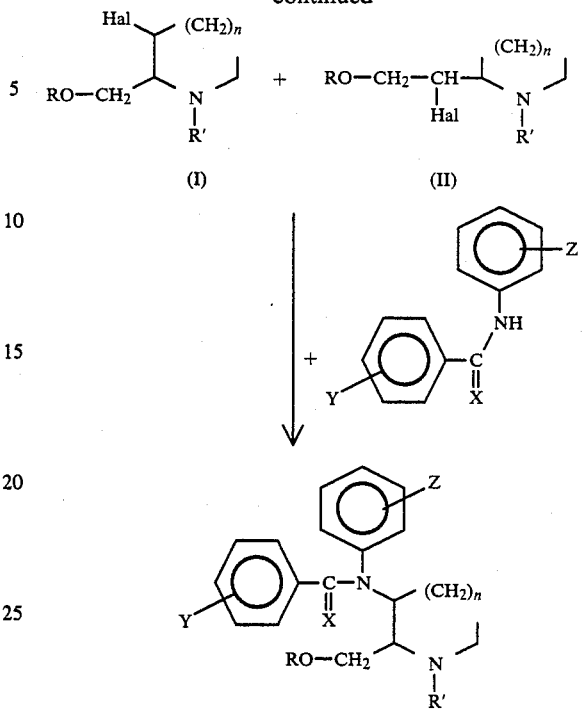

In a first stage, the halogenation of a 2-(α-hydroxy-β-alkoxyethyl)pyrrolidine or -piperidine is performed by means of a customary halogenating agent, such as SOCl$_2$ or PBr$_3$, in a solvent such as chloroform, at a temperature between room temperature and the refluxing temperature of the solvent.

The halogenated derivative formed can have the structure I or the structure II, or alternatively can be a mixture of the two types of structure.

In the first stage, the compound of type I (corresponding to an enlargement of the nitrogen-containing ring) is predominantly obtained when n=2, whereas only compounds of type II are obtained when n=3, the ring enlargement taking place in the second stage.

In the second stage, the product obtained in the previous stage is condensed with a substituted benzylaniline or benzoylaniline preferably in the presence of a strong base such as sodium amide or lithium amide. According to a variant of the process, this second stage can be carried out by phase transfer in the presence of a strong base such as 50-70% sodium hydroxyde solution and a catalyst such as benzyl triethylammonium chloride, a solvent such as toluene or methylene chloride being added if the viscosity of the medium requires it. According to another variant of the process, when X denotes H$_2$, the compounds can also be obtained by reduction of the corresponding homologues (X denotes=O). This reduction can be performed by means of the customary agents such as lithium aluminium hydride or diborane, in a solvent such as ether or tetrahydrofuran. At the end of this stage, the compounds of the invention are extracted from the reaction mixture by the customary methods (for example by extraction with ether or methylene chloride) and then purified by preparative liquid chromatography.

They may also be extracted with the formation and the crystallization of a pharmaceutically acceptable salt.

The examples below illustrate in greater detail the preparation of the compounds of the invention.

EXAMPLE 1

1-methyl-2-[(2-methylpropoxy)methyl]-N-benzyl-N-(3,4-methylenedioxy)phenyl-3-piperidinamine In a first stage, 100 g (0.5 mol) of 1-methyl-2-($\alpha$-hydroxy-$\beta$-isobutoxyethyl)pyrrolidine was introduced into a reactor containing 1 l of anhydrous chloroform, the mixture was then heated to 50° C. and a solution of 82 ml of thionyl chloride in 80 ml of anhydrous chloroform was introduced dropwise, and the mixture was maintained for 4 hours while being heated to the refluxing point of the solvent.

The solvent was then evaporated off and the residue taken up with 1 l of 3% strength hydrochloric acid, then washed with methylene chloride, alkalinized with caustic soda solution and then extracted with methylene chloride. After drying over sodium sulphate and evaporation of the solvent, the residue was distilled and 64 g of 1-methyl-2-isobutoxymethyl-3-chloropiperidine were obtained, of boiling point B.p.$_{0.5}$ 92°–93° C.

In the second stage, 8.35 g (0.045 mol) of 3,4-methylenedioxybenzylaniline and 9.5 g (0.045 mol) of the chlorinated derivative prepared in the first stage, dissolved in 20 ml of toluene, were added in the cold to a suspension of 2.1 g (0.09 mol) of lithium amide in 80 ml of toluene. The reaction was allowed to continue while the mixture was heated to reflux for 5 hours, and the reaction mixture was then allowed to cool and then hydrolysed with 20 ml of saturated aqueous ammonium chloride solution. After filtration, washing with water, drying over sodium sulphate and evaporation of the solvent, the residue was distilled. The product was then purified by preparative liquid chromatography on silica gel, using the following mixture as solvent: Hexane: 85%, ethanol: 7.5%, isopropanol: 7.5%.

2 g of the compound of the title were thereby obtained, of boiling point B.p.$_{0.8}$ 230° C., and having a refractive index n$_D^{20}$=1.5600 and the following elementary analysis:

|  | C % | H % | N % |
|---|---|---|---|
| Theoretical | 73.13 | 8.34 | 6.82 |
| Found | 73.43 | 8.46 | 6.89 |

By way of usual methods, the hydrochloride salt of this compound was also obtained of melting point 148° C.

EXAMPLE 2

1-methyl-2[(2-methylpropoxy)methyl]-N-benzoyl-N-phenyl-3-piperidinamine

In a first stage, 1-methyl-2-isobutoxymethyl-3-chloropiperidine was prepared as described in Example 1.

In the second stage, 20 g of a sodium hydroxide, 20 ml of water, 2 g of benzyltriethylammonium chloride, 20.6 g of benzanilide and 50 ml of toluene were introduced into a reactor, and a solution of 20 g of halogenated derivative prepared in the first stage, in 50 ml of toluene, was then added dropwise.

The mixture was then heated to 85° C. for 3 hours, then allowed to cool and decanted, and the aqueous phase was washed with methylene chloride. The organic phases were combined, whased with water and dried over sodium sulphate, and the solvent was then evaporated off.

34.9 g of a crude residue was thereby otained, and this was stirred for 1 hour with 500 ml of 10% strength hydrochloric acid solution, then neutralized with sodium hydroxide, extracted with methylene chloride and dried. After evaporation of the solvent, 600 ml of 5% strength sodium hydroxide were added and the mixture was heated to 80°–90° C. for 10 hours. After being cooled, the mixture was extracted with methylene chloride, the extract dried over sodium sulphate and the solvent evaporated off.

26.5 g of product was thereby obtained, and this was distilled and the purified by preparative liquid chromatography on silica gel, using the following composition as solvent: Hexane: 84.9%, ethanol: 7.5%, isopropanol: 7.5%, ammonia: 0.1%.

3 g of the compound of the title were thereby obtained, of boiling point B.p.$_{0.7}$ 203°–206° C., of melting point M.p. 80° C. and having the following elementary analysis:

|  | C % | H % | N % |
|---|---|---|---|
| Theoretical | 75.75 | 8.47 | 7.36 |
| Found | 76.11 | 8.57 | 7.35 |

EXAMPLE 3

1-propyl-2-methoxymethyl-N-benzoyl-N-phenyl-3-azepinamine

In a first stage, 32 g (0.16 mol) of 1-propyl-2-($\alpha$-hydroxy-$\beta$-methoxyethyl)piperidine were introduced into a reactor containing 320 ml of anhydrous chloroform, the mixture was brought to 50° C. and 32 ml of thionyl chloride in 32 ml of chlorine were added dropwise, and the mixture was then heated under reflux for 10 h 30 min. After separation and distillation, 24.25 g of 1-propyl-2-($\alpha$-chloro-$\beta$-methoxyethyl)piperidine were obtained, of boiling point B.p.$_{0.5}$ 95° C.

In a second stage, working as described in Example 2, the derivative obtained above was reacted with benzanilide by phase transfer reaction. Starting with 19.75 g (0.09 mol) of chlorinated derivative and 20.6 g (0.1 mol) of benzanilide, after the mixture had been heated for 18 hours at 80°–90° C. and the compound formed then isolated and purified by the means described, 15 g of the compound of the title were obtained, of boiling point B.p.$_{0.4}$ 175°–180° C.

EXAMPLE 4

1-propyl-2-methoxymethyl-N-benzyl-N-phenyl-3-azepinamine 15 g of the compound prepared in Example 3, dissolved in 35 ml of tetrahydrofuran, were added under a nitrogen atmosphere to a reactor containing a suspension of 4.95 g of sodium borohydride in 100 ml of tetrahydrofuran, the temperature being maintained at 0° C. 29.6 ml of boron trifluoride etherate in 39 ml of tetrahydrofuran were then added dropwise. After the reaction medium had been allowed to return to room temperature, 69 ml of 10% strength hydrochloric acid were added. The solvent was then removed by distillation at atmospheric pressure, and the residue cooled and then alkalinized with caustic soda solution and then extracted with methylene chloride. After drying and evaporation of the solvent, the product was distilled, and then purified by preparative liquid chromatography on silica gel, using as solvent 2% strength and then 4% strength methanol in dichloromethane.

5 g of the compound of the title were thereby obtained, of boiling point B.p.$_{0.1}$ 172°–174° C. and having the following elementary analysis:

|  | C % | H % | N % |
|---|---|---|---|
| Theoretical | 78.64 | 9.35 | 7.64 |
| Found | 77.83 | 9.43 | 7.58 |

In the same manner, other compounds according to the invention were prepared, the identification of which is given in Table I below and the physicochemical properties in Table Ia.

TABLE I

| COMPOUND No. | R | R' | X | Y | Z | n |
|---|---|---|---|---|---|---|
| 1 | (CH$_3$)$_2$CH—CH$_2$— | —CH$_3$ | H$_2$ | H | H | 2 |
| 2 | C$_6$H$_{11}$— | —CH$_3$ | O | H | H | 2 |
| 3 (Example 2) | (CH$_3$)$_2$CH—CH$_2$— | —CH$_3$ | O | H | H | 2 |
| 4 (Example 1) | (CH$_3$)$_2$CH—CH$_2$— | —CH$_3$ | H$_2$ | H | 3,4-O—CH$_2$—O— | 2 |
| 5 | (CH$_3$)$_2$CH—CH$_2$— | —CH$_3$ | H$_2$ | H | H | 3 |
| 6 | (CH$_3$)$_2$CH—CH$_2$— | —CH$_3$ | O | H | H | 3 |
| 7 (Example 3) | CH$_3$— | —(CH$_2$)$_2$—CH$_3$ | O | H | H | 3 |
| 8 (Example 4) | CH$_3$— | —(CH$_2$)$_2$—CH$_3$ | H$_2$ | H | H | 3 |
| 9 | (CH$_3$)$_2$CH—CH$_2$— | —CH$_3$ | H$_2$ | 4-CH$_3$ | 4-CH$_3$ | 2 |

TABLE Ia

| COMPOUND No. | n$_D^{20}$ | M.p. °C. | B.p.$_{mmHg}$ | °C. |
|---|---|---|---|---|
| 1 | 1.5560 | / | B.p.$_{0.5}$ | 198–202° C. |
| 2 | / | M.p. 98° C. | B.p.$_{0.5}$ | 220–222° C. |
| 3 (Example 2) | / | M.p. 80° C. | B.p.$_{0.7}$ | 203–206° C. |
| 4 (Example 1) | 1.5600 | Hydrochloride M.p. 148° C. | B.p.$_{0.8}$ | 230° C. |
| 5 | 1.5620 | / | B.p.$_{0.4}$ | 186–192° C. |
| 6 | 1.5460 | / | B.p.$_{0.4}$ | 185–187° C. |
| 7 (Example 3) | / | / | B.p.$_{0.04}$ | 175–180° C. |
| 8 | / | / | B.p.$_{0.1}$ | 172–174° C. |
| 9 | 1.5480 | / | B.p.$_{0.1}$ | 190–195° C. |

The compounds of the invention were shown to possess advantageous antianginal properties, with bradycardic, antitachycardiac and coronary dilatory effects.

The calcium-antagonistic activity was tested according to the technique of Van Rossum (Arch. Int. Pharmacodyn. Ther. 143, 299–330, 1963). To assess the calcium-antagonistic activity at the cardiac level, electrically stimulated rabbit papillary muscle was used (frequency 1.5 Hz; 15 v impulse for 5 ms). For the activity at the vascular level, rabbit aorta cut into a spiral and maintained in a solution devoid of Ca$^{++}$ and enriched with K$^+$ (6 mg/l of KCl) was used. The measurements were performed 15 minutes after adding the compounds to the solution. The traditional parameters of molecular pharmacology are recorded in Table II.

The test of antianginal activity was assessed by investigating the haemodynamic effects in anaesthetized dogs. The animal is anaesthetized with chloralose (100 mg kg$^{-1}$ i.v.) and the following parameters are recorded:

heart rate using subcutaneous ECG electrodes connected to a cardiotachometer, the coronary arterial flow using an electromagnetic flow meter, the blood pressure using a Mikro-tip catheter at the level of the aortic arch, the inotropism, assessed by the left maximal dP/dt, by derivation with respect to time of the left intraventricular pressure recorded using a Mikro-tip catheter in the left ventricle, the antiachycardiac action (inhibition of the positive chronotropic effects of isoprenaline).

These parameters are recorded continuously on a Beckman dynograph. The compounds are administered i.v. at a dose of 5 mg kg$^{-1}$.

The results are expressed as a percentage variation, the duration of action being indicated in brackets, in minutes (Table III).

TABLE II

| COMPOUND | CALCIUM-ANTAGONISTIC ACTIVITY | |
| --- | --- | --- |
| No. | CARDIAC | VASCULAR |
| 1 | 41 | 5.3 |
| 4 | <4 | 6.2 |
| 5 | <4 | 4.7 |
| 8 | <4 | 4.2 |

TABLE III

| | HAEMODYNAMIC ACTIVITY | | | | |
| --- | --- | --- | --- | --- | --- |
| COMPOUND NO. | HEART RATE | CORONARY FLOW | HYPOTENSION | INOTROPISM | ANTI-TACHYCARDIA |
| 1 | −24(>60) | +56(0.5) | −50(10) | −48(>60) | −50(40) |
| 2 | −21(>40) | +103(2) | −73(20) | −76(>39) | −80(>40) |
| 3 | −22(>45) | +75(4) | −50(12) | −71(>40) | −13(17) |
| 4 | −72(>40) | +54 | −60(25) | −69(30) | −65(40) |
| 5 | −11(7) | +27(1) | −36(1) | −24(16) | 0 |
| 8 | −10(23) | −18(4) | 0 | −14(25) | 0 |

These results show that the compounds of the invention have calcium-antagonistic activity on both heart muscle and vascular muscle.

As regards the haemodynamic effects, all these compounds are capable of being, to differing extents, antianginals and/or anti-ischaemics as a result of their bradycardic, coronary dilatory and antitachycardiac activities. Their action on the blood pressure also enables them to be used as antihypertensives.

Among the compounds of the invention, that which shows the greatest value is the compound no. 4, with an exclusively vascular tropism and substantial haemodynamic activities.

The toxicity was assessed orally in mice, and no death was observed up to 500 mg kg$^{-1}$.

This combination of pharmacological properties hence enables the compounds of the invention to be applied in human therapy as a medicinal product for the treatment of cardiovascular disorders such as angina pectoris, ischaemia or hypertension.

The compounds of the invention may be administered enterally or parenterally at daily dosage between 0.5 mg and 10 mg per kg body weight depending on the method of administration.

For the treatment of human beings a daily dosage of 50 up to 500 mg is preferred.

Mixed with suitable auxiliaries the compounds of the invention or salts thereof may be compressed into solid dosage units such as pills, tablets coated tablets, etc. or may be processed into capsules. By means of suitable liquids the compounds may also be applied as an injection, or oral preparation in form of solutions, suspensions or emulsions.

We claim:

1. A compound of the formula:

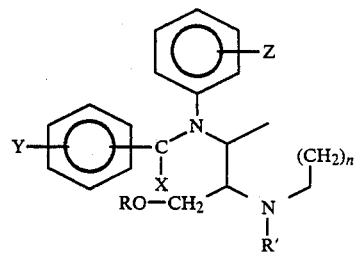

in which R and R' each denote an alkyl radical having 1 to 7 carbon atoms or a cycloalkyl radical having 3 to 7 carbon atoms; X denotes =O or H$_2$; and Y and Z denote hydrogen or one or more radicals chosen from halogeno, hydroxy, straight or branched alkyl having 1 to 6 carbon atoms, alkoxy having 1 to 6 carbon atoms, trifluoromethyl or methylenedioxy; n may assume the values 2 or 3; or a pharmaceutically acceptable salt thereof.

2. A compound according to claim 1, wherein R denotes an isobutyl, methyl or cyclohexyl radical.

3. A compound according to claim 1, wherein R' denotes an methyl or n-propyl radical.

4. Compound according to claim 1, which is 1-methyl-2-((2-methylpropoxy)methyl)-N-benzyl-N-(3,4-methylenedioxy)phenyl-3-piperidinamine, or a pharmaceutically acceptable salt thereof.

5. Pharmaceutical composition for the treatment of cardiovascular disorders comprising an effective amount of a compound according to claim 1 and a pharmaceutically acceptable carrier.

* * * * *